(12) United States Patent
Bartos et al.

(10) Patent No.: US 11,551,800 B1
(45) Date of Patent: Jan. 10, 2023

(54) MULTI-DOSE PACKAGING MEDICATION ADMINISTRATION SYSTEM

(71) Applicant: CVS Pharmacy, Inc., Woonsocket, RI (US)

(72) Inventors: Thomas J. Bartos, Oconomowoc, WI (US); Elise C. Jackson, Winnetka, IL (US); Jorge Seldner, Providence, RI (US); Ian Toner, Boston, MA (US)

(73) Assignee: CVS Pharmacy, Inc., Woonsocket, RI (US)

( * ) Notice: Subject to any disclaimer, the term of this patent is extended or adjusted under 35 U.S.C. 154(b) by 203 days.

(21) Appl. No.: 16/702,951

(22) Filed: Dec. 4, 2019

Related U.S. Application Data (60) Provisional application No. 62/776,623, filed on Dec. 7, 2018.

(51) Int. Cl.
| | |
|---|---|
| *G16H 20/13* | (2018.01) |
| *G16H 15/00* | (2018.01) |
| *G16H 10/60* | (2018.01) |
| *G06K 7/14* | (2006.01) |

(52) U.S. Cl.
CPC ........... *G16H 20/13* (2018.01); *G06K 7/1417* (2013.01); *G16H 10/60* (2018.01); *G16H 15/00* (2018.01)

(58) Field of Classification Search
None
See application file for complete search history.

(56) References Cited

U.S. PATENT DOCUMENTS

| | | | | |
|---|---|---|---|---|
| 8,914,298 | B1* | 12/2014 | Luciano | B65D 75/5888 705/2 |
| 11,152,093 | B1* | 10/2021 | Hopen, Sr | G16H 10/20 |
| 2009/0012820 | A1* | 1/2009 | Bishop | G16H 20/10 705/3 |
| 2011/0000170 | A1* | 1/2011 | Burg | G16H 20/10 53/238 |
| 2014/0350720 | A1* | 11/2014 | Lehmann | A61J 7/0454 221/3 |
| 2019/0267125 | A1* | 8/2019 | Benzel | G16H 20/10 |

OTHER PUBLICATIONS

CVS Health, "Omnicare Multi-Dose Packaging: Improving safety, efficiency, and storage," white paper, May 2, 2019, 4 pgs.

* cited by examiner

*Primary Examiner* — Devin C Hein
(74) *Attorney, Agent, or Firm* — Patent Law Works LLP (57) ABSTRACT

A medication administration and verification system includes scanning a code for a cavity of a multi-dose package to identify at least one previously prescribed medication determined at a time of packaging the at least one previously prescribed medication in the cavity. A list is received in response to the electronically encoded package identifier for at least one currently prescribed medication. At least one visual indicator is displayed respectively corresponding to the at least one currently prescribed medication for the patient for administration during the medication administration event, and a presence or exclusion of each of the currently prescribed medication in the cavity is automatically confirmed for the presence or the exclusion of in the cavity.

20 Claims, 7 Drawing Sheets

JOHN DOE

| FUROSEMIDE 20 MG TABLET | NDC #: 00054429731 | | Morning | Total |
|---|---|---|---|---|
| Rx#: RQ122777-10001-4/10/2018 FUROSEMIDE 20 MG TABLET WHITE Round 54  540 Lot: 2540Q1LA | Dr: ASHRAF FARASAT Mfg: WESTWIND Brand: LASIK | QTY/Card TAKE 1 TAB BY MOUTH EVERY DAY May cause blurred vision. Avoid long exposure to sun. | 7 | 7 |

| DAILY VITE TABLET | NDC #: 00053435470 1 | | Morning | Total |
|---|---|---|---|---|
| Rx#: PQ122785-10001-4/10/2018 DAILY-VITE TABLET red Round Lot: 171499 | Dr: ASHRAF FARASAT Mfg: MIJOSY Brand: Daily Vite | QTY/Card TAKE 1 TAB BY MOUTH EVERY DAY | 7 | 7 |

| ASPIRIN 81 MG TAB CHEW | NDC #: 00904952888 9 | | Morning | Total |
|---|---|---|---|---|
| Rx#: RQ122776-10001-4/10/2018 ASPIRIN ORANGE 81 MG TAB CHEW PEACH Round TCL 334 Lot: 00Q000 | Dr: ASHRAF FARASAT Mfg: MAJOR Brand: Aspirin Chewable | QTY/Card TAKE 1 TAB BY MOUTH EVERY DAY CHEW MED BEFORE SWALLOWING Take with food. Limit alcohol use while taking. "NSAIDS increase GI bleed risk." Report bruising bleeding | 7 | 7 |

| DOCUSATE 100 MG CAPSULE | NDC # 45802043678 | | Morning | Total |
|---|---|---|---|---|
| Rx#: R9122782-10001-4/10/2018 DOCUSATE SODIUM SOFTGEL 100 MG CAPSULE red/white Round Lot: Bca 1600a | Dr: ASHRAF FARASAT Mfg: PERRIGO Brand: DOCUSATE SODIUM | QTY/Card TAKE 1 CAP BY MOUTH EVERY DAY Take with plenty of water. Bitter taste if crushed | 7 | 7 |

| AMLODIPINE 5 MG TABLET | NDC # 59097012705 | | Morning | Total |
|---|---|---|---|---|
| Rx#: R9122785-10001-4/10/2018 AML COPINE DLSYLATE 5 MG TABLET White Round 127 C Lot: oct2148 | Dr: ASHRAF FARASAT Mfg: COPLA Brand: Norvaac | QTY/Card TAKE 1 TAB BY MOUTH EVERY DAY May cause dizziness. | 7 | 7 |

MULTI-DOSE PACKAGING MEDICATION ADMINISTRATION SYSTEM

CROSS REFERENCE TO RELATED APPLICATION(S)

The present application claims priority to U.S. Patent Application No. 62/776,623, titled "Multi-Dose Packaging Medication Administration System," filed Dec. 7, 2018, which is incorporated by reference in its entirety.

TECHNICAL FIELD

The present disclosure generally relates to medication administration, and more particularly relates to systems and methods for verification of currently prescribed medications.

BACKGROUND

Safety and time-efficiency are important factors in the administration of medications, particularly in institutional settings such as assisted living facilities, long-term care facilities, rehabilitation facilities, correctional facilities, hospitals, and others. Residents or patients may take medications multiple times a day, each time they are taking meds they may be taking multiple prescriptions. Caregivers (sometimes called "medication aide aides") may use a med cart stocked with the prescriptions for a group of patients, organized by patient, for a particular administration time (e.g., morning, afternoon, evening, bedtime, breakfast, lunch, dinner, etc.). For safety, caregivers are expected to verify the patient and each medication delivered and administered against a manifest that accurately represents the patient's current medication regimen. For time-efficiency, there is a need to streamline this process, while making it as simple and easy-to-follow for the caregiver as possible.

Electronic medication administration records (eMAR) are software applications used by caregivers to manage and track medication administration during med passes. eMAR has replaced conventional paper logs or manifests in many facilities, enabling caregivers to more easily manage the verification and logging steps of medication administration through a computer, tablet, smartphone, or other electronic interface. eMAR systems may include patient and prescription databases and/or may interface with electronic health record (EHR) systems and other facility management, business, and information systems. eMAR systems may allow medication administration data to be stored, audited, and used to support compliance, billing, and other business and administrative functions for the facility.

Medications are sometimes packaged in multi-dose packages. This may present challenges when there are changes in therapies that may be missed by the medication aide. In the event a medication packaged in multi-dose has been discontinued, the medication needs to be identified and removed at or prior to the point of administration.

Efficiency, simplicity, and ease-of-use in medication administration and verification may also increase the likelihood of adopting similar safety practices by consumers and in-home caregivers.

SUMMARY

The present disclosure describes, among other things, various aspects for reducing medication administration duration and errors. In general, one innovative aspect of the subject matter described in this disclosure may be embodied in a computer-implemented method, comprising: scanning, by a computing device, a code for a cavity of a multi-dose package, the code corresponding to an electronically encoded package identifier configured to identify at least one previously prescribed medication for a patient for administration during a medication administration event, and the cavity including at least one previously prescribed medication as determined at a time of packaging; receiving, by the computing device, a list in response to the electronically encoded package identifier for at least one currently prescribed medication for the patient for administration during the medication administration event; displaying, by the computing device, at least one visual indicator respectively corresponding to the at least one currently prescribed medication for the patient for administration during the medication administration event; automatically confirming, by the computing device, a presence or an exclusion of at least one currently prescribed medication in the cavity; and respectively indicating, by the computing device, at least one visual indicator in response to the confirming the presence or the exclusion of each of the at least one currently prescribed medication in the cavity.

Implementations may include one or more of the following features. A computer-implemented method where indicating each of the at least one visual indicator in response to the confirming of the exclusion of at least one currently prescribed medication in the cavity, further comprises differently indicating as a recently prescribed medication not previously available for packaging in the cavity for each of the at least one visual indicator in response to the exclusion in the cavity of the at least one of the currently prescribed medication. Also, the method further comprises differently indicating as a medication excluded from packaging in the cavity for each of the at least one visual indicator corresponding to at least one of the currently prescribed medication in response to the confirming the exclusion of the at least one currently prescribed medication in the cavity.

Yet, the method further comprises automatically confirming, by the computing device, the presence of the at least one previously prescribed medication in the cavity that is discontinued in the list of the at least one currently prescribed medication; and differently indicating as a medication discontinued as being prescribed for each of the at least one visual indicator respectively corresponding to the at least one previously prescribed medication in the cavity that is discontinued from the list of the at least one currently prescribed medication to not be for administration during the medication administration event.

Further, the method further comprises identifying the at least one previously prescribed medication in the cavity that is discontinued from the list of the at least one currently prescribed medication using respective images of the at least one previously prescribed medication for the patient in the multi-dose package; and receiving, by the computing device, a confirmation that the at least one previously prescribed medication in the cavity that is discontinued from the list of the at least one currently prescribed medication was identified to not be for administration during the medication administration event.

Also, the receiving a list in response to the electronically encoded package identifier, further comprises: accessing prescription data designated by the electronically encoded package identifier to obtain the list for the at least one currently prescribed medication for the patient for administration during the medication administration event. Further, the method comprises filling the cavity of the multi-dose package with the at least one previously prescribed medication; and printing the code on the cavity to identify the at least one previously prescribed medication for the patient.

Another general aspect includes a system comprising: a scanning configuration module configured to scan a code for a cavity of a multi-dose package, the code corresponding to an electronically encoded package identifier configured to identify at least one previously prescribed medication for a patient for administration during a medication administration event, and the cavity including the at least one previously prescribed medication as determined at a time of packaging the at least one previously prescribed medication for the patient in the cavity; a prescription data access module configured to receive a list in response to the electronically encoded package identifier for at least one currently prescribed medication for the patient for administration during the medication administration event; an order interface module configured to display at least one visual indicator respectively corresponding to the at least one currently prescribed medication for the patient for administration during the medication administration event; an auto-confirmation module configured to automatically confirm a presence or an exclusion of each of the at least one currently prescribed medication in the cavity; and a verification queue module configured to respectively indicate each of the at least one visual indicator in response to the confirming the presence or the exclusion of each of the at least one currently prescribed medication in the cavity.

Implementations may include one or more of the following features. A system where the verification queue configured to indicate each of the at least one visual indicator in response to the confirming of the exclusion of at least one currently prescribed medication in the cavity, is further configured to differently indicate as a recently prescribed medication not previously available for packaging in the cavity for each of the at least one visual indicator in response to the exclusion in the cavity of the at least one of the currently prescribed medication.

The verification queue module is further configured to differently indicate as a medication excluded from packaging in the cavity for each of the at least one visual indicator corresponding to at least one of the currently prescribed medication in response to the confirming the exclusion of the at least one currently prescribed medication in the cavity. The auto-confirmation module is further configured to: automatically confirm the presence of the at least one previously prescribed medication in the cavity that is discontinued in the list of the at least one currently prescribed medication; and differently indicate as a medication discontinued as being prescribed for each of the at least one visual indicator respectively corresponding to the at least one previously prescribed medication in the cavity that is discontinued from the list of the at least one currently prescribed medication to not be for administration during the medication administration event.

The verification queue module is further configured to: identify the at least one previously prescribed medication in the cavity that is discontinued from the list of the at least one currently prescribed medication using respective images of the at least one previously prescribed medication for the patient in the multi-dose package; and receive a confirmation that the at least one previously prescribed medication in the cavity that is discontinued from the list of the at least one currently prescribed medication was identified to not be for administration during the medication administration event.

The prescription data access module is further configured to, in response to receiving the list, access prescription data designated by the electronically encoded package identifier to obtain the list for the at least one currently prescribed medication for the patient for administration during the medication administration event. The system further comprising a pharmacy dispensing system configured to: fill the cavity of the multi-dose package with the at least one previously prescribed medication; and print the code on the cavity to identify the at least one previously prescribed medication for the patient.

Another general aspect includes a system comprising: means for scanning, by a computing device, a code for a cavity of a multi-dose package, the code corresponding to an electronically encoded package identifier configured to identify at least one previously prescribed medication for a patient for administration during a medication administration event, and the cavity including the at least one previously prescribed medication as determined at a time of packaging the at least one previously prescribed medication for the patient in the cavity; means for receiving, by the computing device, a list in response to the electronically encoded package identifier for at least one currently prescribed medication for the patient for administration during the medication administration event; means for displaying, by the computing device, at least one visual indicator respectively corresponding to the at least one currently prescribed medication for the patient for administration during the medication administration event; means for automatically confirming, by the computing device, a presence or an exclusion of each of the at least one currently prescribed medication in the cavity; and means for respectively indicating, by the computing device, each of the at least one visual indicator in response to the confirming the presence or the exclusion of each of the at least one currently prescribed medication in the cavity.

Implementations may include one or more of the following features. A system where the means for indicating each of the at least one visual indicator in response to the confirming the exclusion of the at least one currently prescribed medication in the cavity, further comprises: means for differently indicating as a recently prescribed medication not previously available for packaging in the cavity for each of the at least one visual indicator in response to the exclusion in the cavity of the at least one of the currently prescribed medication.

The system further comprises means for differently indicating as a medication excluded from packaging in the cavity for each of the at least one visual indicator corresponding to at least one of the currently prescribed medication in response to the confirming the exclusion of the at least one currently prescribed medication in the cavity. The system further comprises means for automatically confirming, by the computing device, the presence of the at least one previously prescribed medication in the cavity that is discontinued in the list of the at least one currently prescribed medication; and means for differently indicating as a medication discontinued as being prescribed for each of the at least one visual indicator respectively corresponding to the at least one previously prescribed medication in the cavity that is discontinued from the list of the at least one currently prescribed medication to not be for administration during the medication administration event.

The system further comprises means for identifying the at least one previously prescribed medication in the cavity that is discontinued from the list of the at least one currently prescribed medication using respective images of the at least one previously prescribed medication for the patient in the multi-dose package; and means for receiving, by the computing device, a confirmation that the at least one previously prescribed medication in the cavity that is discontinued from the list of the at least one currently prescribed medication was identified to not be for administration during the medication administration event. The system where the means for receiving a list in response to the electronically encoded package identifier, further comprises: means for accessing prescription data designated by the electronically encoded package identifier to obtain the list for the at least one currently prescribed medication for the patient for administration during the medication administration event.

It should be understood that the language used in the present disclosure has been principally selected for readability and instructional purposes, and not to limit the scope of the subject matter disclosed herein.

BRIEF DESCRIPTION OF THE DRAWINGS

The present disclosure is illustrated by way of example, and not by way of limitation in the figures of the accompanying drawings in which like reference numerals are used to refer to similar elements.

DETAILED DESCRIPTION

Multi-dose packaging is when a pharmacy presorts a resident's medications by the day of the week and time of day a medication will be administered. Multi-dose packaging may presort a patient's medications by the prescribed time of day for some or all of a resident's regimen of tablets and capsules for a period of time, such as one week. Prescribed maintenance tablets and capsules are packaged together into a multi-dose packages (MDP) by time of administration (sometime referred to as "med pass") by the pharmacy for these medications in a compacted package for Monday-Sunday. For example, a resident may receive a 7-day booklet prefilled with the resident's regimen of tablets and capsules. The booklet may contain four med pass times (morning, afternoon, evening, bedtime) for each of the seven days of the week. The start consumption date may be Monday. Twenty-eight prefilled plastic bubbles or blisters corresponding to each med pass may be included in the booklet and detach from one another along a perforated edge. Each med pass package may include a plurality of prescriptions being administered on that particular date and time. Each med pass package may also include an electronically readable code, such as a barcode, quick response (QR) code, an Aztec barcode, radio frequency identifier (RFID), etc.

Safety is an important consideration in use of multi-dose packaging. According to at least one study, 70% of medication errors in Assisted Living homes result from a medication being administered at the wrong time. Medication administration may be governed by five core principles: right resident, right medication, right dose, right route, and the right time.

Multi-dose packaging may be improved by easy to follow visual cues. For example, each med pass package may include color-coded med pass indicators (e.g. yellow for morning, gray for afternoon, orange for evening, blue for bedtime, etc.) with associated med pass icons (e.g. images of the rising sun, night stars, etc. to indicate the time of day). Another example may be including high resolution pill images on the packaging, such as inside the booklet cover, that clearly define pill color, shape, and markings to indicate which medication is which.

Each multi-dose package (MDP) may include an electronically readable code that is readable by an eMAR application with integrated code reading capabilities, such as an image or laser-based barcode scanner. The electronically readable code may be used to validate a resident is receiving the appropriate medication. For example, a barcode may encode the prescription numbers for each medication in the multidose package or provide a unique identifier that may be used to access patient, med pass, prescription, and/or other information from an eMAR database or related EHR system. In some embodiments, printed on each individual, detachable cavity prefilled with medications is a square barcode that has embedded text identifying the orders of each medication packaged within the cavity.

In an example use, a medication aide may register the time and resident being administered within the eMAR interface. Next, the medication aide may scan the barcode on the back of the detachable cavity of the med pass package. The eMAR may then use the encoded information to retrieve and confirm the expected medications have been packaged in the blister. The medication aide's scan of the barcode may queue the medications into the facility's eMAR interface. The scan may inform the medication aide if the resident's medication regimen extends beyond what has been packaged in the multi-dose package. The eMAR interface may then display all medications associated with the med pass, including both the medications in the multi-dose package and other medications that have not been packed within the multi-dose package (due to storage or handling restrictions, prescription changes, etc.). Those in the multi-dose package may be automatically confirmed, while others may be verified by separate scans or manual entry (such as clicking on a verification icon for the medication on the eMAR interface). Further, if a barcode on the cavity is damaged or otherwise does not properly scan, backup barcodes may be included in the med pass package.

Scanning verification from the multi-dose package may provide triple confirmation for the staff. If additional medications need to be administered a medication aide is notified. If the wrong multi-dose package (MDP) booklet has been pulled, a medication aide will be notified. If the morning is scanned instead of bedtime, a medication aide will be notified. By scanning the barcode, the medication aide may have confidence that the medications packaged are the medications the eMAR is expecting for administration.

Scanning verification also supports changes in medications, which may occur due to prescription changes after the multi-dose package (MDP) prefilled booklet is received. The first fill of a new medication may be sent on in a single dose package (e.g. bingo card). The multi-dose package barcode scan may provide a visual and/or auditory reminder to the medication aide to ensure the resident is receiving their entire regimen, including the new and separately packaged medication. A resident may be prescribed a new medication that has not yet been packaged in the multi-dose booklet. When the med tech scans the barcode, any medications that were excluded from the multi-dose will not be confirmed, but they will be identified and queued (e.g., displayed for administration). The medication aide may be informed by the display that there are additional medications outside of the multi-dose packaging to be administered.

The scan may indicate any changes to therapy of the packaged medications. In the instance the change of therapy is a discontinued med, the scan will indicate to the med tech there is a packaged discontinued medication that needs to be removed from the multi-dose package (MDP). If a medication that has been packaged in the multi-dose package (MDP) has been discontinued, the scan may inform the med tech of the medication change though an indicator or alert not to administer the discontinued medication from the multi-dose package (MDP). The med tech is empowered to ensure the discontinued medication is not administered to the patient and may be provided visual references on the package and/or eMAR interface for identifying the medication to be removed. The medication aide is able to identify which medication will need to be removed prior to administration guided by high resolution pill images provided on a medication identification insert that has been printed on the packaging to support proper identification.

Compatibility with multi-dose packaging with med pass scanning may include configuration of an eMAR system to receive, parse, and use information encoded in the packaging or accessible using the coded information. In some embodiments, the eMAR should handle multi-dose packages with pills from different prescriptions where the packaging is labeled by the multi-dose packaging technology and prescriptions labeled and shipped by the pharmacy that are not part of the multi-dose set of order and may or may not include individual dose bar codes. During medication administration at the facility for each resident, facility eMAR and EHR systems that are matching prescriptions to resident based on the barcode scanning should be able to scan a variety of coded packages.

The multi-dose pharmacy automation machine may create the barcode using the value of the prescription numbers included in the packaging file for electronic prescription orders with certain packaging requests, such as express requests for multi-dose packaging or as a default for multi-day, multi-med orders (e.g. 7-day packaging requests). For example, if a med pass cavity has four orders or medications in it, the barcode may be a comma separated list 142, based on the prescription data 132, with four prescription number entries (e.g. Barcode="R123456, R789012, R345678, R901234"). Other coding schemes may be used and an eMAR/EHR configuration may support multiple code schemes, including different schemes for multi-dose packaging versus single dose packaging.

Multi-dose package (MDP) may be assembled in booklets for simple storage and organization. Each blister to be administered may have perforated edges that can easily be detached from the booklet. An oversized bubble size, exceeding the volume occupied by the medications themselves, gives the space for a simple punch-out that will be easy on staff when they are opening-up perhaps hundreds of medication packaging every day. This may also assist consumers, patients who self-administer, and caregivers with physical limitations in accessing the medications. Individual med pass packages may be compact enough to transport without being so small they are easily dropped or lost (e.g., like individual pills or bingo card cells). Users may benefit by being able to discreetly bring packaged medications on an outing.

Approximately one to two multi-dose booklets per resident will replace approximately eight individual bingo cards that a resident may previously have received. The compact booklet facilitates an organized medication storage space for the community and simplified process for locating the correct multi-dose package booklet. Booklets may have flexibility to be neatly stacked in a med storage room or arranged with the spines facing forward in a med cart. Med carts may be customized to accommodate, organize, and display the booklets needed for that med cart and time period.

For example, a resident's name and room number may be printed in bold letters on the spine and arranged facing toward the medication aide. A medication aide may scan to locate resident name and extract the booklet for administration. In addition, other medications on separate bingo cards (as needed) may be accommodated inside the cover of the booklet for ease of organization and administration.

Time administering medications in long-term care may be substantial. This time has a real cost for facilities and erodes staff time that could be spent enjoying the presence of a community's residents' or addressing other pressing needs for the facility. Medication administration using multi-dose packs as described herein may reduce the time med aides spend administering medication by more than 25%.

With reference to the figures, reference numbers may be used to refer to components found in any of the figures, regardless whether those reference numbers are shown in the figure being described. Further, where a reference number includes a letter referring to one of multiple similar components (e.g., component 000a, 000b, and 000n), the reference number may be used without the letter to refer to one or all of the similar components.

Figure 1:
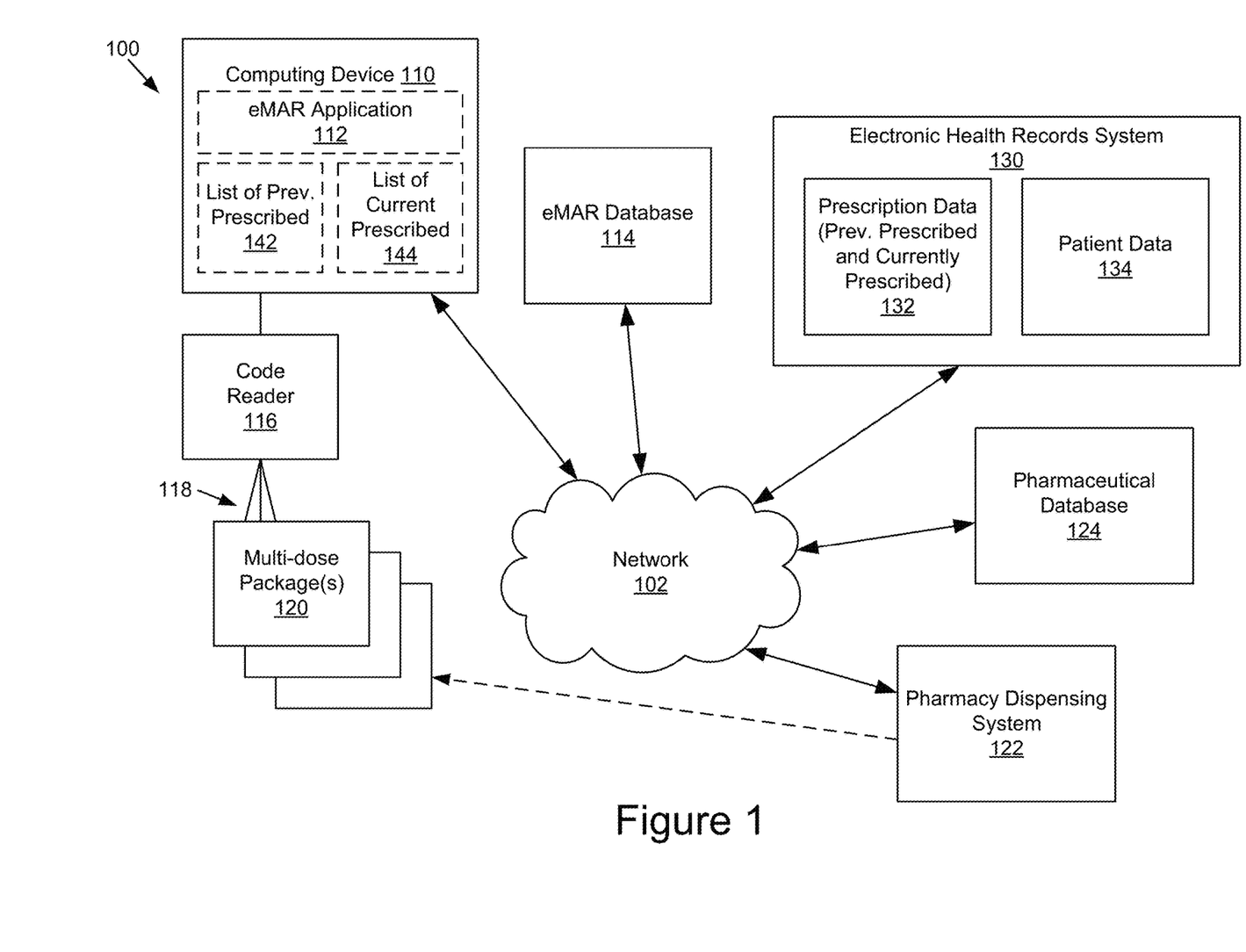
FIG. 1 is a block diagram of an example system for medication administration using a multi-dose packaging system.

FIG. 1 is a block diagram of an example system 100 for medication administration using multi-dose packaging. System 100 may include a computing device 110, an eMAR database 114, a pharmacy dispensing system 122, a pharmaceutical database 124, and an electronic health records system 130, each of which may be electronically communicatively coupled via a network 102 for interaction with one another, although other system configurations are possible including other devices, systems, and networks. For example, each device, database, and system may include, be part of, or be hosted on one or more computing devices.

In the example shown, computing device 110 may host an eMAR application 112 and be communicatively connected to code reader 116 for reading a coded identifier, such as a bar code, from multi-dose package(s) 120 using a signal 118, such as light reflected from a bar code. In some embodiments, eMAR application 112 may be in communication with eMAR database 114 and/or prescription data 132 and patient data 134 in EHR system 130 for accessing prescription and patient information for verifying medications during a med pass.

For example, computing device 110 may be a med pass computing device, such as a laptop, tablet, smartphone, or similar device used in conjunction with a med cart for distributing medication in an institutional setting. eMAR application 112, eMAR database 114, and/or EHR system 130 may be components of a facility management system or healthcare information network.

In another example, computing device 110 may be a computing device used by a consumer, patient, in-home caregiver (personal or service provider), or other person administering medications outside of an institutional setting. eMAR application 112 may be an app or similar program loaded on a personal computer, tablet, smartphone, or other smart device that accesses one or more cloud-based resources for personal healthcare management, including eMAR database 114.

Multi-dose package(s) 120 may be filled based on prescription and patient information and receive the coded identifier for each med pass package in the multi-dose packages. For example, pharmacy dispensing system 122 may be maintained by a pharmacy or pharmacy system that provides multi-dose packaged medications to institutions and/or consumers.

The network 102 may include any number of networks and/or network types. For example, the network 102 may include, but is not limited to, one or more local area networks (LANs), wide area networks (WANs) (e.g., the Internet), virtual private networks (VPNs), wireless wide area network (WWANs), WiMAX® networks, personal area networks (PANs) (e.g., Bluetooth® communication networks), various combinations thereof, etc. These private and/or public networks may have any number of configurations and/or topologies, and data may be transmitted via the networks using a variety of different communication protocols including, for example, various Internet layer, transport layer, or application layer protocols. For example, data may be transmitted via the networks using TCP/IP, UDP, TCP, HTTP, HTTPS, DASH, RTSP, RTP, RTCP, VOIP, FTP, WS, WAP, SMS, MMS, XMS, IMAP, SMTP, POP, WebDAV, or other known protocols.

Figure 2A:
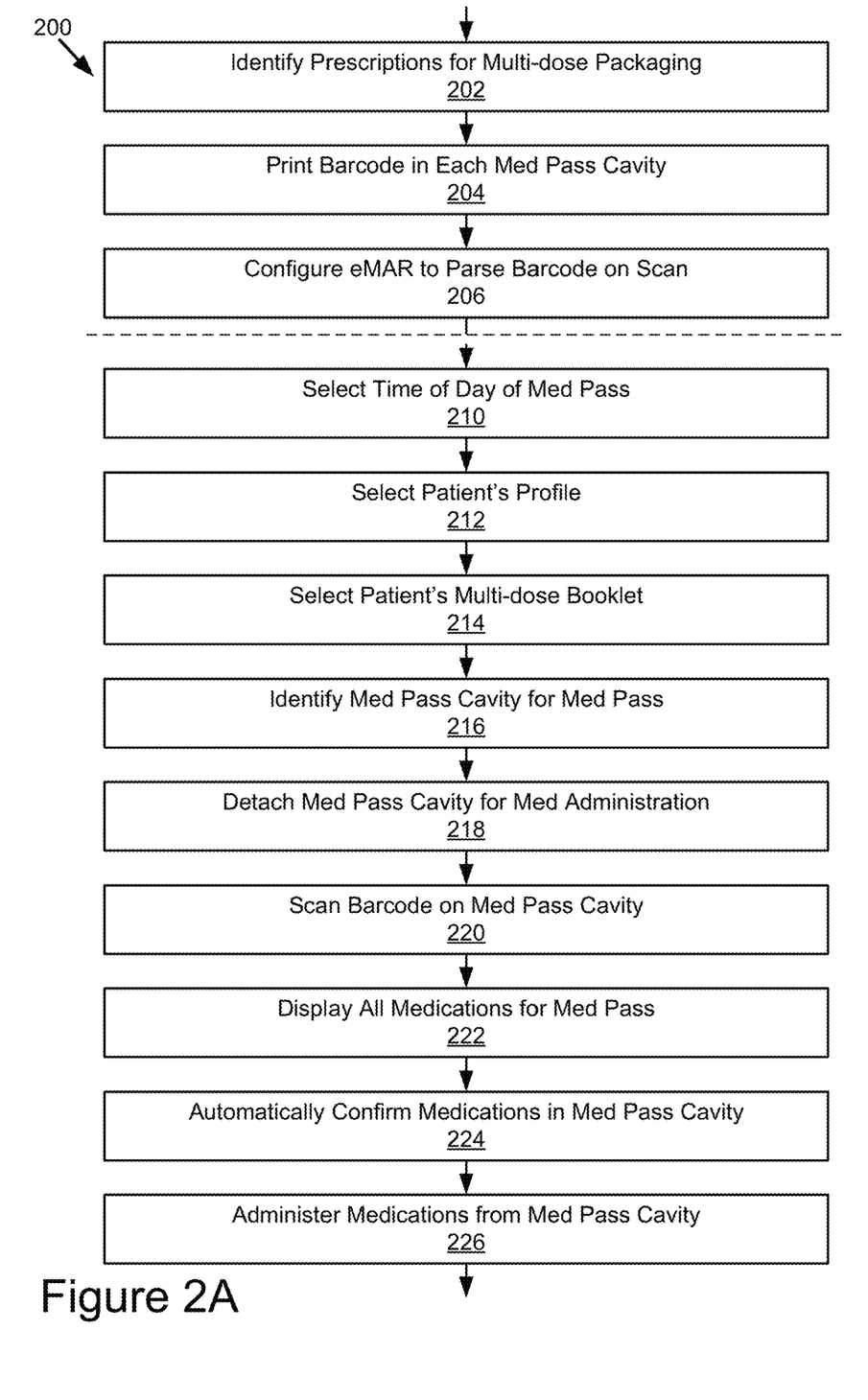
FIGS. 2A and 2B are flowcharts of example methods for medication administration using a multi-dose packaging system.

FIG. 2A is a flowchart of an example method 200 for medication administration using multi-dose packaging.

At 202, a plurality of prescriptions are identified for multi-dose packaging for at least one patient. Multiple medications are packaged according to the dosage schedules in their respective prescriptions and grouped according to their target administration time or med pass in a med pass cavity. At least one cavity of the multi-dose package is filled with at least one previously prescribed medication.

At 204, a barcode is printed on each med pass cavity that encodes information about the medications contained therein (e.g. prescription numbers) and/or a unique identifier from which such information can be accessed. The code is printed on the cavity to identify the at least one previously prescribed medication for the patient.

At 206, an eMAR system or application is configured to parse the barcode on each med pass package when scanned. In some embodiments, configuring the eMAR may include defining one or more administrative steps, workflows, and/or interfaces that may be navigated by a user, such as a medication aide, during medication administration. For example, the eMAR may include a series of administrative steps completed for each patient during a med pass with regard to patient verification, medication aide verification, inventory, billing, and/or other activities integrated into med pass operations for the facility.

For each med pass, at 210 the time of day of the med pass is selected and at 212 the patient's profile is selected, such as using an eMAR interface. At 214, the patient's multi-dose booklet is selected, a med pass cavity for the particular med pass is identified at 216, and the identified med pass cavity is detached for medication administration at 218. At 220, the barcode on the med pass cavity is scanned to identify the medications in the med pass cavity and trigger medication verification workflows in the eMAR system. At 222, all medications for the med pass are displayed on the interface of the eMAR systems. At 224, the eMAR system automatically confirms medications in the med pass cavity based on the scan. At 226, the medications from the med pass cavity are administered to the patient.

Figure 2B:
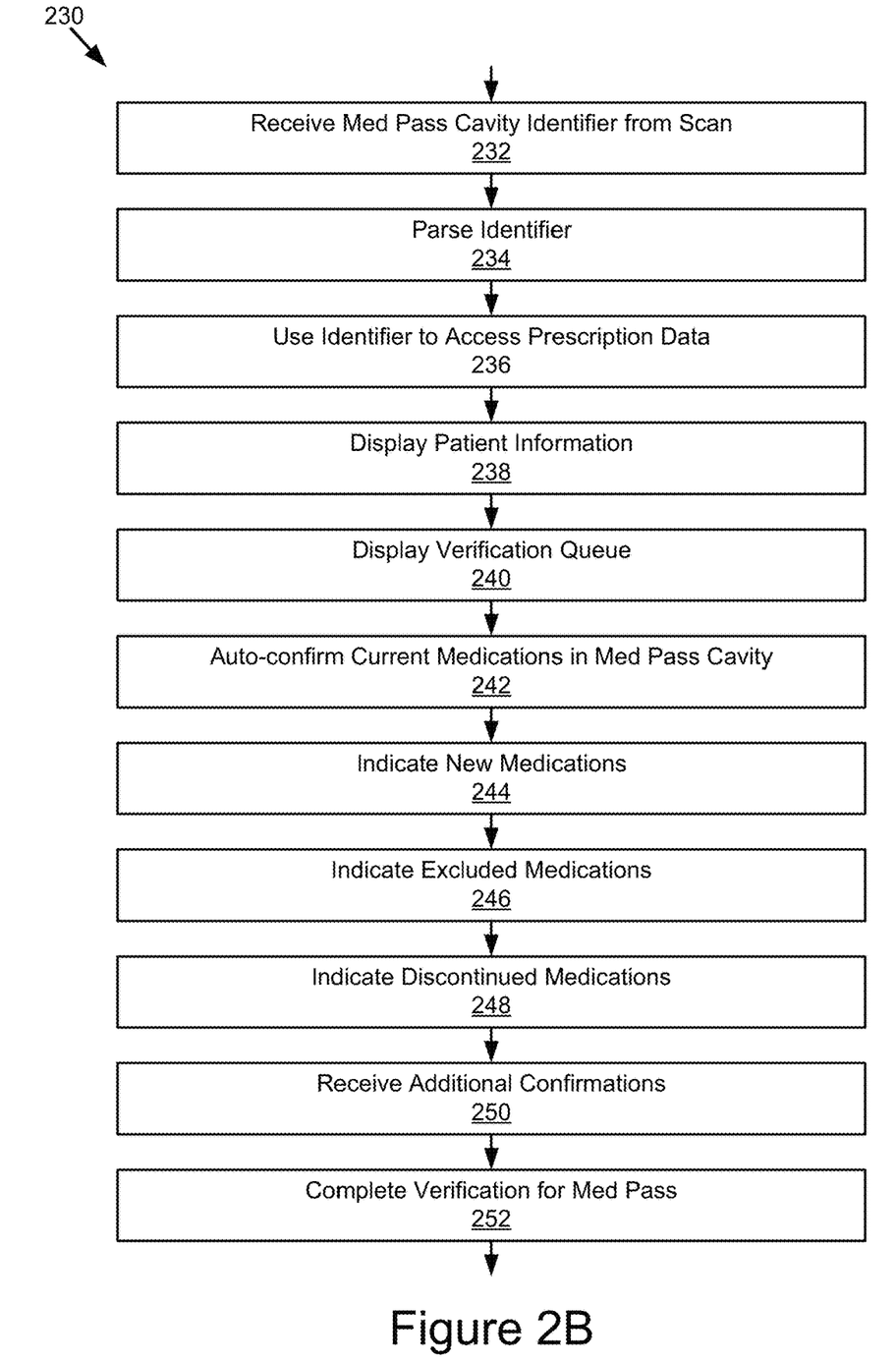

FIG. 2B is a flowchart of an example method 230 for an eMAR system automating medication administration using a multi-dose package. In some embodiments, method 230 may be used in conjunction with method 200.

At 232, an electronically encoded med pass cavity identifier is received from a scan of the med pass cavity identifier on a med pass cavity. The computing device 110 scans a code for a cavity of a multi-dose package 120 where the code corresponds to an electronically encoded package identifier configured to identify at least one previously prescribed medication for a patient for administration during a medication administration event. The cavity includes the at least one previously prescribed medication as determined at a time of packaging of the at least one previously prescribed medication for the patient in the cavity.

At 234, the med pass cavity identifier may be parsed to determine one or more encoded identifiers, such as a plurality of prescription numbers.

At 236, the identifier is used to access prescription data, such as the list of orders applicable to the specific med pass, along with the medication names, descriptions, visual identifiers, administration notes/instructions/warnings, and other information available through the system. The computing device 110 accesses prescription data designated by the electronically encoded package identifier to obtain the list 144, based on the prescription data 132, for the at least one currently prescribed medication for the patient for administration during the medication administration event. The computing device 110 receives the list in response to the electronically encoded package identifier for at least one currently prescribed medication for the patient for administration during the medication administration event.

At 238, patient information is displayed on the interface for visual confirmation by the user, such as based on a prior selection of the patient or responsive to the identifier.

At 240, a verification queue of all medications to be administered to the patient during the med pass may be displayed, such as a series of icons, table entries, or similar indicators corresponding to each of the medications for administration and verification. The computing device 112 displays at least one visual indicator respectively corresponding to the at least one currently prescribed medication for the patient for administration during the medication administration event.

At 242, all current medications in the med pass cavity (as represented by the med pass cavity identifier) are automatically confirmed in the verification queue and include a visual indicator to that effect, such as a colored highlight or check mark. The computing device 112 automatically confirms a presence or an exclusion of each of the at least one currently prescribed medication in the cavity. The computing device 112 respectively indicates each of the at least one visual indicator in response to the confirming the presence or the exclusion of each of the at least one currently prescribed medication in the cavity.

At 244, any new medications not included in the med pass cavity, such as order originating after the multi-dose package was filled, but still scheduled for administration in the med pass may be indicated as such. In response to the confirming the exclusion of at least one currently prescribed medication in the cavity, the at least one visual indicator differently indicates the recently prescribed medication as not being previously available for packaging in the cavity.

At 246, any excluded medications not included in the med pass cavity, such as medications with different storage or handling requirements, but still scheduled for administration in the med pass may be indicated as such. The computing device 112 differently indicates as a medication excluded from packaging in the cavity for each of the at least one visual indicator corresponding to at least one of the currently prescribed medication in response to the confirming the exclusion of the at least one currently prescribed medication in the cavity.

At 248, any discontinued medications included in the med pass cavity, such as any discontinued after the multi-dose package was filled, and no longer scheduled for administration in the med pass, may be indicated as such and may include additional warnings or notifications to assure that the discontinued medication is not administered. The computing device 112 automatically confirms the presence of the at least one previously prescribed medication in the cavity that is discontinued in the list of the at least one currently prescribed medication. The computing device 112 differently indicates as a medication discontinued as being prescribed for each of the at least one visual indicator respectively corresponding to the at least one previously prescribed medication in the cavity that is discontinued from the list of the at least one currently prescribed medication to not be for administration during the medication administration event.

At 250, any additional confirmations needed for the new and excluded medications and/or acknowledgements of non-administration of the discontinued medication may be received based on additional scans or other confirmation methods, such as clicking or tapping an icon associated with the medication on the interface. Further, further confirmations and protections may include identifying at least one previously prescribed medication in the cavity that is discontinued from the list of the currently prescribed medications using respective images of the previously prescribed medication in the multi-dose package. The computing device may then receive a confirmation that the previously prescribed medication in the cavity that is discontinued from the list of currently prescribed medications was identified to not be administered during the medication administration event.

At 252, verification for med pass is complete and the user may proceed to the next patient.

Figure 3:
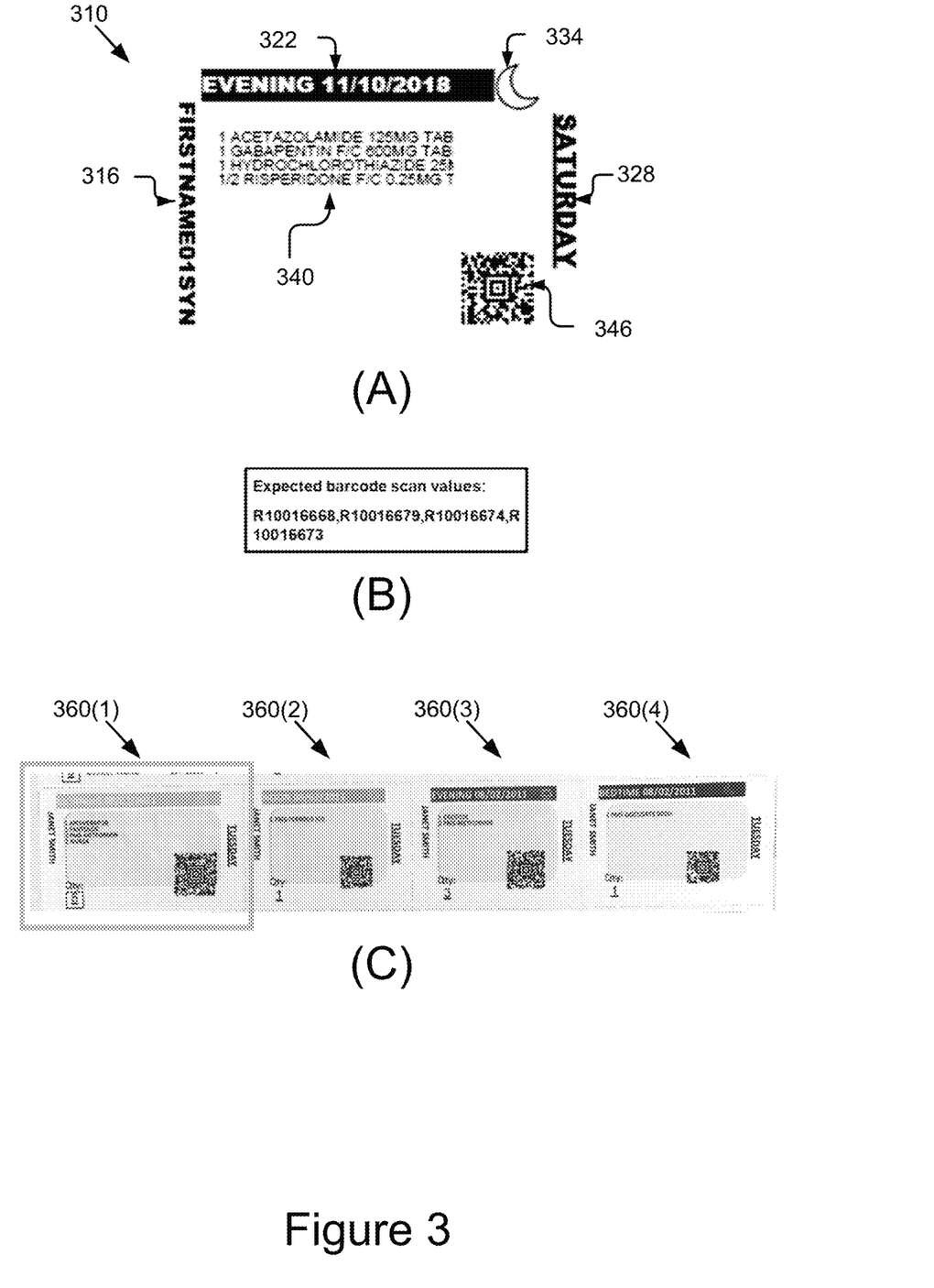
FIG. 3 illustrates example scannable images for identifying medications in a multi-dose packaging system.

FIG. 3 illustrates example scannable images for identifying medications in a multi-dose packaging system. FIG. 3(A) illustrates an example label 310 on a packet of a multi-dose package. The label 310 may include various information, examples of which include a patient name 316, a day/date/time-of-day indicator 322, a day of the week 328, a time of day indicator 334, dosage and medication indicators 340, and a barcode or code 346. Multiple medications are packaged according to the dosage schedules in their respective prescriptions and grouped according to their target administration time or med pass in a med pass cavity. At least one cavity of the multi-dose package is filled with at least one previously prescribed medication. The barcode or code is printed on each med pass cavity that encodes information about the medications contained therein (e.g. prescription numbers) and/or a unique identifier from which such information can be accessed. The code 346 is printed on the cavity to identify the at least one previously prescribed medication for the patient. While one form of code is illustrated, the code may take the form of an electronically readable code, such as a barcode, quick response (QR) code, radio frequency identifier (RFID), etc.

The multi-dose pharmacy automation machine may create the barcode using the value of the prescription numbers included in the packaging file for electronic prescription orders with certain packaging requests, such as express requests for multi-dose packaging or as a default for multi-day, multi-med orders (e.g. 7-day packaging requests). For example, a barcode may encode the prescription numbers for each medication in the multidose package or provide a unique identifier that may be used to access patient, med pass, prescription, and/or other information from an eMAR database or related EHR system. In some embodiments, printed on each individual, detachable cavity prefilled with medications is a square barcode that has embedded text identifying the orders of each medication packaged within the cavity.

FIG. 3(B) is a list 142 of the previously prescribed medications for a patient. The resulting scan values are coded to correspond to specific medications. For example, if a med pass cavity has four orders or medications in it, the barcode may be a comma separated list with four prescription number entries (e.g. Barcode="R10016668, R10016679, R10016674, R10016673"). Other coding schemes may be used and an eMAR/EHR configuration may support multiple code schemes, including different schemes for multi-dose packaging versus single dose packaging.

FIG. 3(C) illustrates a series of individual, detachable cavities 360(1-4) prefilled with medications. As illustrated, printed on each individual, detachable cavity prefilled with medications is a square barcode that has embedded text identifying the orders of each medication packaged within the cavity.

Figure 4:
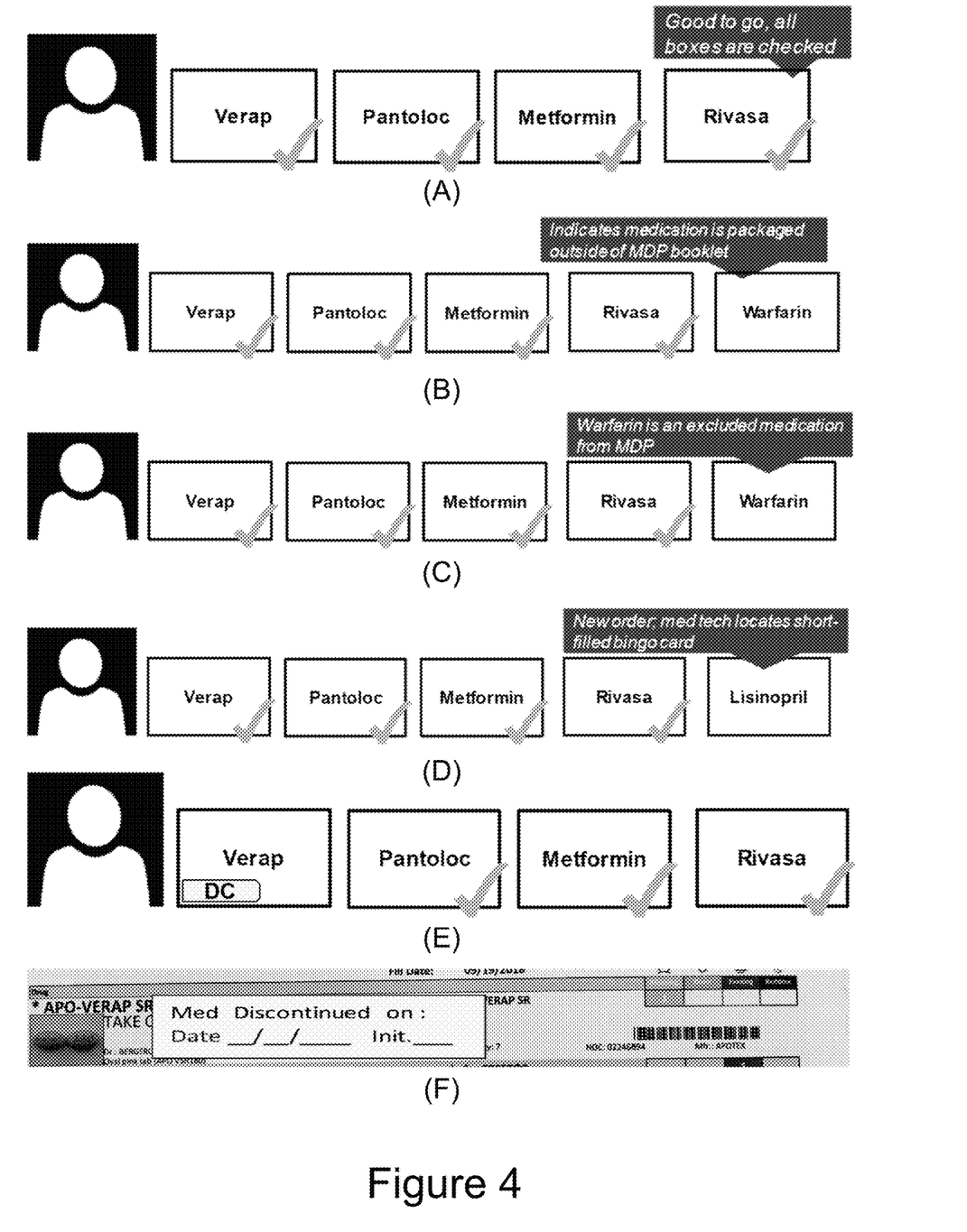
FIG. 4 illustrates example scenario indications of a presence or an exclusion of each of the currently prescribed medications with respect to a previously prescribed medications packaged in a multi-dose packaging system.

FIG. 4 illustrates example scenario indications of a presence or an exclusion of each of the currently prescribed medications with respect to a previously prescribed medications packaged in a multi-dose packaging system.

In the scenario illustrated in FIG. 4(A), the indicators are set in response to the scan of the barcode on the cavity. In the present scenario, each of the previously prescribed medications is included within the cavity as indicated, for example, by check marks or some other indicia, such as a color indicator, textual indicator, audible indicator, etc. Accordingly, the medication aide may complete administration by retrieving all of the prescribed medications for the patient from the cavity.

In the scenario illustrated in FIG. 4(B), the indicators are set in response to the scan of the barcode on the cavity. In the present scenario, each of the previously prescribed medications, with the exception of one medication, is included within the cavity as indicated, for example, by check marks or some other indicia, such as a color indicator, textual indicator, audible indicator, etc. The excluded medication is differently indicated as a medication excluded from packaging in the cavity, but was previously or originally prescribed and filled by a pharmacy. The excluded medication may be differently indicated using, for example, the absence of a confirming checkmark. Further, a note as illustrated, may indicate that the medication is packaged outside of the cavity of the multi-dose package. Therefore, the different indication confirms the exclusion of the at least one currently prescribed medication in the cavity. Accordingly, the medication aide may complete administration by retrieving all of the prescribed medications from the cavity and from a source outside of the cavity of the multi-dose package. Medications not suitable for packaging may include liquids, or fragile (e.g., orally disintegrable) tablets, etc.

In the scenario illustrated in FIG. 4(C), the indicators are set in response to the scan of the barcode on the cavity. In the present scenario, each of the previously prescribed medications, with the exception of one medication, is included within the cavity as indicated, for example, by check marks or some other indicia, such as a color indicator, textual indicator, audible indicator, etc. The excluded medication is differently indicated as a medication excluded from packaging in the cavity, but was not previously or originally prescribed and filled by a pharmacy at the time of the packaging of the multi-dose package. The excluded medication may be differently indicated using, for example, by the absence of a confirming checkmark. Further, a note, as illustrated, may indicate that the medication is an excluded medication from the multi-dose package. Therefore, the different indication confirms the exclusion of the at least one currently prescribed medication in the cavity. Accordingly, the medication aide may complete administration by retrieving all of the prescribed medications from the cavity and from a source outside of the cavity of the multi-dose package.

In the scenario illustrated in FIG. 4(D), the indicators are set in response to the scan of the barcode on the cavity. In the present scenario, each of the previously prescribed medications, with the exception of one medication, is included within the cavity as indicated, for example, by check marks or some other indicia, such as a color indicator, textual indicator, audible indicator, etc. The excluded medication is differently indicated as a medication excluded from packaging in the cavity, but is currently prescribed and filled by a pharmacy. The excluded medication may be differently indicated using, for example, by the absence of a confirming checkmark. Further, a note, as illustrated, may indicate that the medication is packaged outside of the cavity of the multi-dose package. Therefore, the different indication confirms, using the at least one visual indicator corresponding to at least one of the currently prescribed medication, that at least one currently prescribed medication is excluded from the cavity and needs to be located and administered from another source (e.g., 'bingo card') in response to a recently filled prescription. Accordingly, the medication aide may complete administration by retrieving all of the prescribed medications from the cavity and from a source outside of the cavity of the multi-dose package.

In the scenario illustrated in FIG. 4(E), the indicators are set in response to the scan of the barcode on the cavity. In the present scenario, each of the previously prescribed medications is included within the cavity as indicated, however, one of the medications is differently indicated as being a previously prescribed medication that is discontinued. Discontinuation of a medication may be based on an updated prescription from a prescribing physician indicating the medication is no longer to be administered to the patient. While the non-discontinued medications may be indicated, for example, by check marks or some other indicia, such as a color indicator, textual indicator, audible indicator, etc., the discontinued medication is differently indicated, for example, using words or initials such as "DC" for discontinued and is not to be administered during the medication administration event.

Furthermore, FIG. 4(F) illustrates further information that may be provided to the medication aide in the form of an image of the discontinued medication to assist the medication aide in identifying the discontinued medication from other non-discontinued medications in the cavity. Yet further, a label, such as illustrated in FIG. 4(F) may be applied to a booklet containing the multi-dose package containing the discontinued medication.

Figure 5:
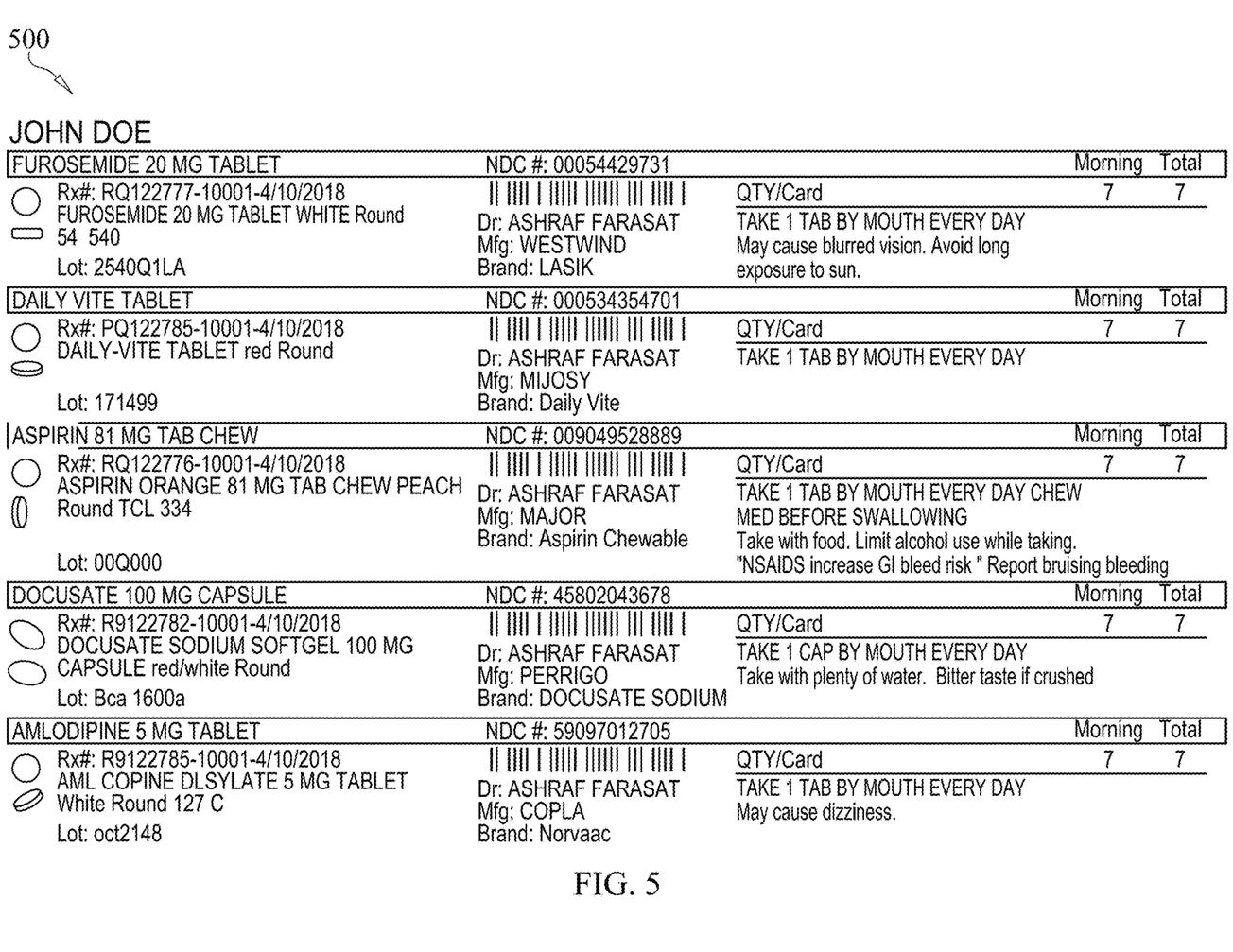
FIG. 5 illustrates an example medication identification insert in a multi-dose packaging system.

FIG. 5 illustrates an example medication identification insert 500 in a multi-dose packaging system. The medication identification insert 500 may include images, dosages, identification markings, and scannable codes used to assist a medication aide in the identification of medications that form a part of previously prescribed medications. The medication identification insert 500 may be further used by the medication aide to further confirm medications in a cavity of the multi-dose package.

Figure 6:
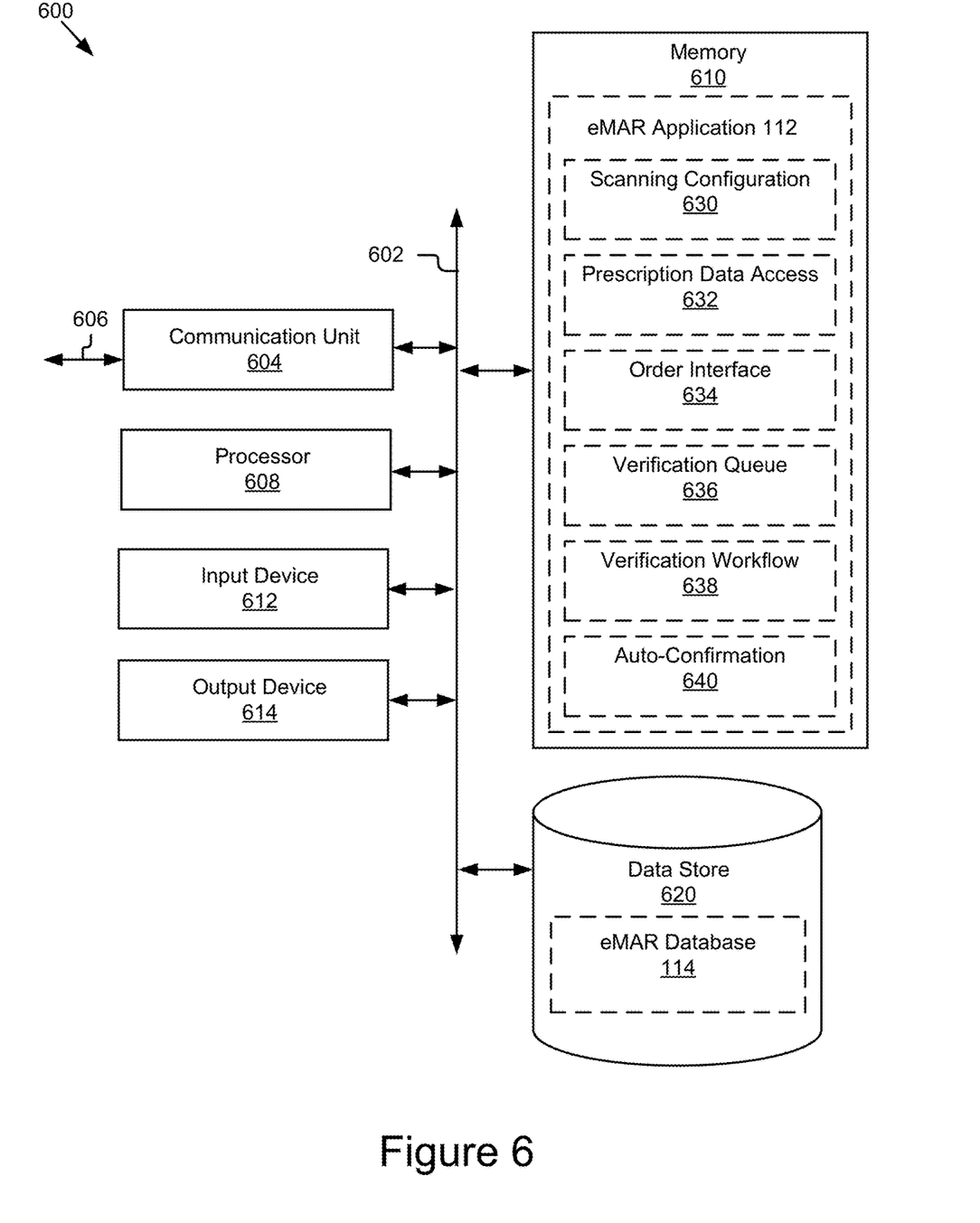
FIG. 6 is a block diagram of an example computing system.

FIG. 6 is a block diagram of an example computing device 600, which may represent a computing device configured to implement modules depicted in FIG. 1, such as eMAR application 112 and eMAR database 114, depending on the implementation.

As depicted, the computing system 600 may include a processor 608, a memory 610, a communication unit 604, an output device 614, an input device 612, and a data store 620, which may be communicatively coupled by a communication bus 602. The computing system 600 depicted in FIG. 6 is provided by way of example and it should be understood that it may take other forms and include additional or fewer components without departing from the scope of the present disclosure. For instance, various components of the computing device may be coupled for communication using a variety of communication protocols and/or technologies including, for instance, communication buses, software communication mechanisms, computer networks, etc. While not shown, the computing system 600 may include various operating systems, sensors, additional processors, and other physical configurations. The processor 608, memory 610, communication unit 604, etc., are representative of one or more of these components.

The processor 608 may execute software instructions by performing various input, logical, and/or mathematical operations. The processor 608 may have various computing architectures to method data signals (e.g., CISC, RISC, etc.). The processor 608 may be physical and/or virtual, and may include a single core or plurality of processing units and/or cores. In some implementations, the processor 608 may be coupled to the memory 610 via the bus 602 to access data and instructions therefrom and store data therein. The bus 602 may couple the processor 608 to the other components of the computing system 600 including, for example, the memory 610, the communication unit 604, the input device 612, the output device 614, and the data store 620.

The memory 610 may store and provide data access to the other components of the computing system 600. The memory 610 may be included in a single computing device or a plurality of computing devices. In some implementations, the memory 610 may store instructions and/or data that may be executed by the processor 608. For example, the memory 610 may store eMAR application 112. The memory 610 is also capable of storing other instructions and data, including, for example, an operating system, hardware drivers, other software applications, databases, etc. The memory 610 may be coupled to the bus 602 for communication with the processor 608 and the other components of computing system 600.

In the example shown, eMAR application 112 includes a plurality of modules related to operation of eMAR application 112 in accordance with the systems and methods described above. These modules are shown by example and may not include all modules in eMAR application 112. eMAR application 112 may include scanning configuration 630 for receiving and parsing encoded information from a scan, prescription data access 632 for accessing prescription and/or patient information based on the information from the scan, order interface 634 for displaying order information and verification indicators to a user, verification queue 636 for organizing and displaying information related to each medication in a med pass, verification workflow 638 for defining the options and actions for navigating the verification process during a med pass, and auto-confirmation 640 for automatically confirming specific medications based on the encoded information and/or information accessed.

The scanning configuration module 630 may be configured to scan a code for a cavity of a multi-dose package, with the code corresponding to an electronically encoded package identifier configured to identify at least one previously prescribed medication for a patient for administration during a medication administration event, and the cavity including the at least one previously prescribed medication as determined at a time of packaging the at least one previously prescribed medication for the patient in the cavity.

The prescription data access module 632 may be configured to receive a list in response to the electronically encoded package identifier for at least one currently prescribed medication for the patient for administration during the medication administration event. The prescription data access module 632 may be further configured to, in response to receiving the list, access prescription data designated by the electronically encoded package identifier to obtain the list for the at least one currently prescribed medication for the patient for administration during the medication administration event.

The order interface module 634 may be configured to display at least one visual indicator respectively corresponding to the at least one currently prescribed medication for the patient for administration during the medication administration event.

The auto-confirmation module 640 may be configured to automatically confirm a presence or an exclusion of each of the at least one currently prescribed medication in the cavity. The auto-confirmation module 640 may be further configured to automatically confirm the presence of the at least one previously prescribed medication in the cavity that is discontinued in the list of the at least one currently prescribed medication. The auto-confirmation module 640 may be yet further configured to differently indicate as a medication discontinued as being prescribed for each of the at least one visual indicator respectively corresponding to the at least one previously prescribed medication in the cavity that is discontinued from the list of the at least one currently prescribed medication to not be for administration during the medication administration event.

The verification queue module 636 may be configured to respectively indicate each of the at least one visual indicator in response to confirming the presence or the exclusion of each of the at least one currently prescribed medication in the cavity. The verification queue module 636 may be configured to indicate each of the at least one visual indicator in response to the confirming of the exclusion of at least one currently prescribed medication in the cavity, is further configured to differently indicate as a recently prescribed medication not previously available for packaging in the cavity for each of the at least one visual indicator in response to the exclusion in the cavity of the at least one of the currently prescribed medication. The verification queue module 636 may be further configured to differently indicate as a medication excluded from packaging in the cavity for each of the at least one visual indicator corresponding to at least one of the currently prescribed medication in response to the confirming the exclusion of the at least one currently prescribed medication in the cavity. The verification queue module 636 may be further configured to identify the at least one previously prescribed medication in the cavity that is discontinued from the list of the at least one currently prescribed medication using respective images of the at least one previously prescribed medication for the patient in the multi-dose package. The verification queue module 636 may be further configured to receive a confirmation that the at least one previously prescribed medication in the cavity that is discontinued from the list of the at least one currently prescribed medication was identified to not be for administration during the medication administration event.

The memory 610 may include a non-transitory computer-usable (e.g., readable, writeable, etc.) medium, which can be any non-transitory apparatus or device that can contain, store, communicate, propagate or transport instructions, data, computer programs, software, code, routines, etc., for processing by or in connection with the processor 608. In some implementations, the memory 610 may include one or more of volatile memory and non-volatile memory (e.g., RAM, ROM, hard disk, optical disk, etc.). It should be understood that the memory 610 may be a single device or may include multiple types of devices and configurations.

The bus 602 can include a communication bus for transferring data between components of a computing device or between computing devices, a network bus system including the network 102 or portions thereof, a processor mesh, a combination thereof, etc. In some implementations, eMAR application 112 and various other components operating on the computing device 600 (operating systems, device drivers, etc.) may cooperate and communicate via a communication mechanism included in or implemented in association with the bus 602. The software communication mechanism can include and/or facilitate, for example, inter-method communication, local function or procedure calls, remote procedure calls, an object broker (e.g., CORBA), direct socket communication (e.g., TCP/IP sockets) among software modules, UDP broadcasts and receipts, HTTP connections, etc. Further, any or all of the communication could be secure (e.g., SSH, HTTPS, etc.).

The communication unit 604 may include one or more interface devices (I/F) for wired and wireless connectivity among the components of the system 100. For instance, the communication unit 604 may include, but is not limited to, various types of known connectivity and interface options. The communication unit 604 may be coupled to the other components of the computing system 600 via the bus 602. The communication unit 604 can provide other connections to the network 102 and to other entities of the system 100 using various standard communication protocols.

The input device 612 may include any device for inputting information into the computing system 600. In some implementations, the input device 612 may include one or more peripheral devices. For example, the input device 612 may include a keyboard, a pointing device, microphone, an image/video capture device (e.g., camera), RFID scanner, barcode scanner (image or laser), a touch-screen display integrated with the output device 614, etc. The output device 614 may be any device capable of outputting information from the computing system 600. The output device 614 may include one or more of a display (LCD, OLED, etc.), a printer, a haptic device, audio reproduction device, touch-screen display, a remote computing device, etc. In some implementations, the output device is a display which may display electronic images and data output by a processor of the computing system 600 for presentation to a user, such as the processor 608 or another dedicated processor.

The data store 620 may include information sources for storing and providing access to data. In some implementations, the data store 620 may store data associated with a database management system (DBMS) operable on the computing system 600. For example, the DBMS could include a structured query language (SQL) DBMS, a NoSQL DMBS, various combinations thereof, etc. In some instances, the DBMS may store data in multi-dimensional tables comprised of rows and columns, and manipulate, e.g., insert, query, update and/or delete, rows of data using programmatic operations.

The data stored by the data store 620 may be organized and queried using various criteria including any type of data stored by them, such as a user identifier, a prescription identifier, user attributes, patient attributes, facility attributes, medical administration records, time/location data, etc. The data store 620 may include data tables, databases, or other organized collections of data. In the example shown, some or all of eMAR database 114 may be stored in data store 620 and may include patient information, prescription information, package or dose identifiers, medical administration records, and other information for use by eMAR application 112.

The data store 620 may be included in the computing system 600 or in another computing system and/or storage system distinct from but coupled to or accessible by the computing system 600. The data stores 620 can include one or more non-transitory computer-readable mediums for storing the data. In some implementations, the data stores 620 may be incorporated with the memory 610 or may be distinct therefrom.

The components 604, 608, 610, 612, and/or 614 may be communicatively coupled by the bus 602 and/or the processor 608 to one another and/or the other components of the computing system 600. In some implementations, the components 604, 608, 610, 612, and/or 614 may include computer logic (e.g., software logic, hardware logic, etc.) executable by the processor 608 to provide their acts and/or functionality. In any of the foregoing implementations, these components 604, 608, 610, 612, and/or 614 may be adapted for cooperation and communication with the processor 608 and the other components of the computing system 600.

In the above description, for purposes of explanation, numerous specific details are set forth in order to provide a thorough understanding of the present disclosure. However, it should be understood that the technology described herein can be practiced without these specific details. Further, various systems, devices, and structures are shown in block diagram form in order to avoid obscuring the description. For instance, various implementations are described as having particular hardware, software, and user interfaces. However, the present disclosure applies to any type of computing device that can receive data and commands, and to any peripheral devices providing services.

In some instances, various implementations may be presented herein in terms of algorithms and symbolic representations of operations on data bits within a computer memory. An algorithm is here, and generally, conceived to be a self-consistent set of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

To ease description, some elements of the system and/or the methods are referred to using the labels first, second, third, etc. These labels are intended to help to distinguish the elements but do not necessarily imply any particular order or ranking unless indicated otherwise.

It should be borne in mind, however, that all of these and similar terms are to be associated with the appropriate physical quantities and are merely convenient labels applied to these quantities. Unless specifically stated otherwise as apparent from the following discussion, it is appreciated that throughout this disclosure, discussions utilizing terms including "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Various implementations described herein may relate to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, including, but is not limited to, any type of disk including floppy disks, optical disks, CD-ROMs, and magnetic disks, read-only memories (ROMs), random access memories (RAMs), EPROMs, EEPROMs, magnetic or optical cards, flash memories including USB keys with non-volatile memory or any type of media suitable for storing electronic instructions, each coupled to a computer system bus.

The technology described herein can take the form of an entirely hardware implementation, an entirely software implementation, or implementations containing both hardware and software elements. For instance, the technology may be implemented in software, which includes but is not limited to firmware, resident software, microcode, etc. Furthermore, the technology can take the form of a computer program object accessible from a computer-usable or computer-readable medium providing program code for use by or in connection with a computer or any instruction execution system. For the purposes of this description, a computer-usable or computer readable medium can be any non-transitory storage apparatus that can contain, store, communicate, propagate, or transport the program for use by or in connection with the instruction execution system, apparatus, or device.

A data processing system suitable for storing and/or executing program code may include at least one processor coupled directly or indirectly to memory elements through a system bus. The memory elements can include local memory employed during actual execution of the program code, bulk storage, and cache memories that provide temporary storage of at least some program code in order to reduce the number of times code must be retrieved from bulk storage during execution. Input or I/O devices (including but not limited to keyboards, displays, pointing devices, etc.) can be coupled to the system either directly or through intervening I/O controllers.

Network adapters may also be coupled to the system to enable the data processing system to become coupled to other data processing systems, storage devices, remote printers, etc., through intervening private and/or public networks. Wireless (e.g., Wi-Fi™) transceivers, Ethernet adapters, and Modems, are just a few examples of network adapters. The private and public networks may have any number of configurations and/or topologies. Data may be transmitted between these devices via the networks using a variety of different communication protocols including, for example, various Internet layer, transport layer, or application layer protocols. For example, data may be transmitted via the networks using transmission control protocol/Internet protocol (TCP/IP), user datagram protocol (UDP), transmission control protocol (TCP), hypertext transfer protocol (HTTP), secure hypertext transfer protocol (HTTPS), dynamic adaptive streaming over HTTP (DASH), real-time streaming protocol (RTSP), real-time transport protocol (RTP) and the real-time transport control protocol (RTCP), voice over Internet protocol (VOIP), file transfer protocol (FTP), WebSocket (WS), wireless access protocol (WAP), various messaging protocols (SMS, MMS, XMS, IMAP, SMTP, POP, WebDAV, etc.), or other known protocols.

Finally, the structure, algorithms, and/or interfaces presented herein are not inherently related to any particular computer or other apparatus. Various general-purpose systems may be used with programs in accordance with the teachings herein, or it may prove convenient to construct more specialized apparatus to perform the required method blocks. The required structure for a variety of these systems will appear from the description above. In addition, the specification is not described with reference to any particular programming language. It will be appreciated that a variety of programming languages may be used to implement the teachings of the specification as described herein.

The foregoing description has been presented for the purposes of illustration and description. It is not intended to be exhaustive or to limit the specification to the precise form disclosed. Many modifications and variations are possible in light of the above teaching. As will be understood by those familiar with the art, the specification may be embodied in other specific forms without departing from the spirit or essential characteristics thereof. Likewise, the particular naming and division of the modules, routines, features, attributes, methodologies and other aspects are not mandatory or significant, and the mechanisms that implement the specification or its features may have different names, divisions and/or formats. Furthermore, the modules, routines, features, attributes, methodologies and other aspects of the disclosure can be implemented as software, hardware, firmware, or any combination of the foregoing. Also, wherever a component, an example of which is a module, of the specification is implemented as software, the component can be implemented as a standalone program, as part of a larger program, as a plurality of separate programs, as a statically or dynamically linked library, as a kernel loadable module, as a device driver, and/or in every and any other way known now or in the future. Additionally, the disclosure is in no way limited to implementation in any specific programming language, or for any specific operating system or environment.

The invention claimed is:

1. A computer-implemented method, comprising:
    scanning, by a computing device, a code for a cavity of a multi-dose package, the code corresponding to an electronically encoded package identifier, the electronically encoded package identifier based on an expected content of the cavity and including an explicit encoding of a plurality of prescription numbers representing medication administered to a patient during a medication administration event as determined at a time of packaging, the medication administered to the patient during the medication administration event including the expected content of the cavity and an excluded medication, the expected content of the cavity including a first medication for the patient for administration during the medication administration event, the cavity including the first medication, the excluded medication prescribed at the time of packaging the first medication in the cavity but excluded from the cavity;
    receiving, by the computing device, a list, in response to the electronically encoded package identifier, of currently prescribed medication for the patient for administration during the medication administration event;
    displaying, by the computing device, visual indicators respectively corresponding to each currently prescribed medication for administration during the medication administration event, the currently prescribed medication for administration during the medication administration event including the first medication and the excluded medication;
    automatically confirming, by the computing device, a presence in or an exclusion from the cavity of each currently prescribed medication for administration during the medication administration event; and
    respectively indicating, by the computing device in the display, the presence in or the exclusion from the cavity of each currently prescribed medication for administration during the medication administration event.

2. The computer-implemented method of claim 1, wherein indicating the exclusion of a currently prescribed, second medication from the cavity, further comprises:
    differently indicating, as a recently prescribed medication not previously available for packaging in the cavity, a visual indicator associated with a second medication, the second medication not prescribed at the time of packaging the first medication in the cavity.

3. The computer-implemented method of claim 1, further comprising:
    differently indicating the excluded medication, as a medication excluded from packaging in the cavity, in response to the confirming the exclusion of the excluded medication.

4. The computer-implemented method of claim 1, further comprising:
    automatically confirming, by the computing device, the presence of a previously prescribed medication in the cavity that is discontinued in the list of currently prescribed medication; and
    differently indicating, as a medication discontinued and not for administration during the medication administration event, the previously prescribed medication in the cavity that is discontinued from the list of currently prescribed medication.

5. The computer-implemented method of claim 4, further comprising:
    identifying the previously prescribed medication in the cavity that is discontinued from the list of the currently prescribed medication using an image of the previously prescribed medication that is discontinued but packaged in the cavity of the multi-dose package; and
    receiving, by the computing device, a confirmation that the previously prescribed medication in the cavity that is discontinued from the list of currently prescribed medication was identified to not be for administration during the medication administration event.

6. The computer-implemented method of claim 1, wherein the electronically encoded package identifier includes a concatenation of a first prescription identifier representing the first medication and a second prescription identifier representing a second medication, and the list includes the first medication and the second medication, wherein the second medication is the excluded medication.

7. The computer-implemented method of claim 1, further comprising:
filling the cavity of the multi-dose package; and
printing the code on the cavity.

8. A system, comprising:
one or more processors; and
a memory storing instructions that, when executed by the one or more processors, cause the system to:
scan a code for a cavity of a multi-dose package, the code corresponding to an electronically encoded package identifier, the electronically encoded package identifier based on an expected content of the cavity and including an explicit encoding of a plurality of prescription numbers representing medication to be administered to a patient during a medication administration event as determined at a time of packaging, the medication administered to the patient during the medication administration event including the expected content of the cavity and an excluded medication, the expected content of the cavity including a first medication for the patient for administration during the medication administration event, the cavity including the first medication, the excluded medication prescribed at the time of packaging the first medication in the cavity but excluded from the cavity;
receive a list, in response to the electronically encoded package identifier, of currently prescribed medication for the patient for administration during the medication administration event;
display at least one visual indicator respectively corresponding to each currently prescribed medication for the patient for administration during the medication administration event, the currently prescribed medication for administration during the medication administration event including the first medication and the excluded medication;
automatically confirm a presence in or an exclusion from the cavity of each currently prescribed medication; and
respectively indicate the presence in or the exclusion from the cavity of each currently prescribed medication in a display.

9. The system of claim 8, wherein indicating the exclusion of a currently prescribed, second medication from the cavity, instructions, when executed by the one or more processors, further cause the system to:
differently indicate, as a recently prescribed medication not previously available for packaging in the cavity, a visual indicator associated with a second medication, the second medication not prescribed at the time of packaging the first medication in the cavity.

10. The system of claim 8, wherein the instructions, when executed by the one or more processors, further cause the system to:
differently indicate the excluded medication, as a medication excluded from packaging in the cavity, in response to the confirming the exclusion of the excluded medication.

11. The system of claim 8, wherein the instructions, when executed by the one or more processors, further cause the system to:
automatically confirm the presence of a previously prescribed medication in the cavity that is discontinued in the list of the currently prescribed medication; and
differently indicate, as a medication discontinued and not for administration during the medication administration event, the previously prescribed medication in the cavity that is discontinued from the list of currently prescribed medication.

12. The system of claim 11, wherein the instructions, when executed by the one or more processors, further cause the system to:
identify the previously prescribed medication in the cavity that is discontinued from the list of the currently prescribed medication using an image of the previously prescribed medication that is discontinued but packaged in the cavity of the multi-dose package; and
receive a confirmation that the previously prescribed medication in the cavity that is discontinued from the list of currently prescribed medication was identified to not be for administration during the medication administration event.

13. The system of claim 8, wherein the electronically encoded package identifier includes a concatenation of a first prescription identifier representing the first medication and a second prescription identifier representing a second medication, and the list include the first medication and the second medication, wherein the second medication is the excluded medication.

14. The system of claim 8, wherein the instructions, when executed by the one or more processors, further cause the system to:
fill the cavity of the multi-dose package; and
print the code on the cavity.

15. A system, comprising:
means for scanning, by a computing device, a code for a cavity of a multi-dose package, the code corresponding to an electronically encoded package identifier, the electronically encoded package identifier based on an expected content of the cavity and including an explicit encoding of a plurality of prescription numbers representing medication to be administered to a patient during a medication administration event as determined at a time of packaging, the medication administered to the patient during the medication administration event including the expected content of the cavity and an excluded medication, the expected content of the cavity including a first medication for the patient for administration during the medication administration event, the cavity including the first medication, the excluded medication prescribed at the time of packaging the first medication in the cavity but excluded from the cavity;
means for receiving, by the computing device, a list, in response to the electronically encoded package identifier, of currently prescribed medication for the patient for administration during the medication administration event;
means for displaying, by the computing device, at least one visual indicator respectively corresponding to each currently prescribed medication for the patient for administration during the medication administration event, the currently prescribed medication for administration during the medication administration event including the first medication and the excluded medication;

means for automatically confirming, by the computing device, a presence in or an exclusion from the cavity of each currently prescribed medication in the cavity; and means for indicating, by the computing device, the presence in or the exclusion from the cavity of each currently prescribed medication.

16. The system of claim 15, wherein the means for indicating exclusion of currently prescribed medication from the cavity, further comprises:

means for differently indicating, as a recently prescribed medication not previously available for packaging in the cavity, a visual indicator associated with a second medication, the second medication not prescribed at the time of packaging the first medication in the cavity.

17. The system of claim 15, further comprising:

means for differently indicating the excluded medication, as a medication excluded from packaging in the cavity, in response to the confirming the exclusion of the excluded medication.

18. The system of claim 15, further comprising:

means for automatically confirming, by the computing device, the presence of a previously prescribed medication in the cavity that is discontinued in the list of currently prescribed medication; and means for differently indicating as a medication discontinued and not for administration during the medication administration event, the previously prescribed medication in the cavity that is discontinued from the list of currently prescribed medication.

19. The system of claim 18, further comprising:

means for identifying the previously prescribed medication in the cavity that is discontinued from the list of currently prescribed medication using an image of the previously prescribed medication that is discontinued but packaged in the cavity of the multi-dose package; and means for receiving, by the computing device, a confirmation that the previously prescribed medication in the cavity that is discontinued from the list of currently prescribed medication was identified to not be for administration during the medication administration event.

20. The system of claim 15, wherein the electronically encoded package identifier includes a concatenation of a first identifier associated with a first medication and a second identifier associated with a second medication, and the list including the first medication and the second medication, wherein the second medication is the excluded medication.

* * * * *